United States Patent [19]

Ohta et al.

[11] Patent Number: 4,567,890

[45] Date of Patent: Feb. 4, 1986

[54] PAIR OF BIPOLAR DIATHERMY FORCEPS FOR SURGERY

[76] Inventors: Tomio Ohta, 1-22-25 Tezukayama, Abeno-ku; Noboru Funatsu, Akuto III 1008, 15-4 Doyamacho, Kita-ku, both of Osaka, Japan

[21] Appl. No.: 638,562

[22] Filed: Aug. 7, 1984

[30] Foreign Application Priority Data

Aug. 9, 1983 [JP] Japan .................................. 58-145952

[51] Int. Cl.$^4$ ............................................. A61B 17/36
[52] U.S. Cl. ............................. 128/303.13; 128/321
[58] Field of Search ....................... 128/303.13, 303.17, 128/321–324, 750; 604/30, 31, 34; 433/30, 31, 87, 96, 100; 222/526, 527

[56] References Cited

U.S. PATENT DOCUMENTS

| | | | |
|---|---|---|---|
| 3,019,790 | 2/1962 | Militana | 128/322 |
| 3,916,909 | 11/1975 | Kletschka et al. | 128/321 |
| 4,041,952 | 8/1977 | Morrison et al. | 128/303.13 |
| 4,049,002 | 9/1977 | Kletschka et al. | 128/321 |

OTHER PUBLICATIONS

"Common–Bileduct Forceps", The Lancet, Sep. 4, 1965, vol. II, p. 476, by Wilson.

Primary Examiner—Edward M. Coven
Assistant Examiner—Max F. Hindenburg
Attorney, Agent, or Firm—Moonray Kojima

[57] ABSTRACT

A pair of bipolar diathermy forceps used for surgery having two arms electrically insulated from each other and adapted to keep opening their tips usually, comprising a tube which extends toward the inside tips of the arms and which is mounted along a groove, the said groove is provided on either or both of the arms, an elongate section which follows the said groove, an operational section inserted between two arms whereby a hole of the tube is open, when the said arms are closed and is closed when they are open, and a pouring section of physiological saline which is connected to the end of the tube. Irrigation is started when the arms are closed and is stopped when they are open automatically. When the tissue is held by the tips of arms and supplied with the current, the coagulation is caused by the high frequency conducted, whereby the control of hemorrhage is completed. The frequent saline irrigation of the work area in microsurgery and the dilution of a little bleeding can be obtained.

3 Claims, 4 Drawing Figures

FIG.1  FIG.2  FIG.3
FIG.4
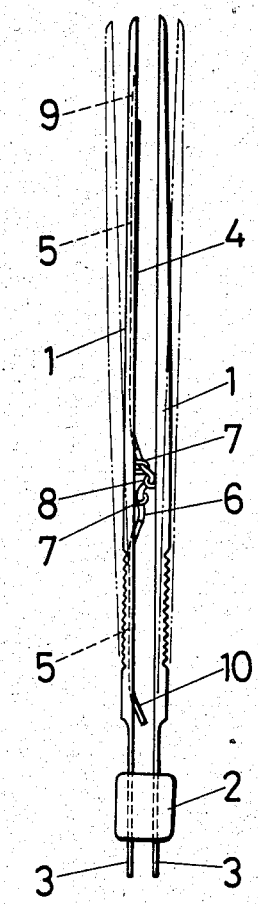
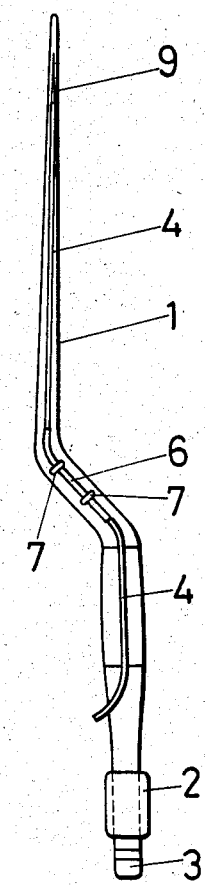
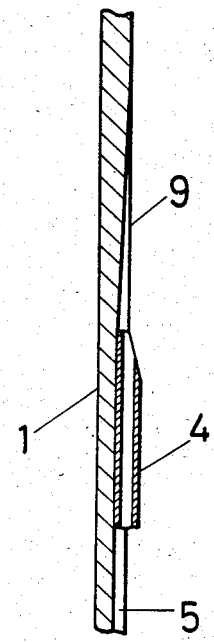
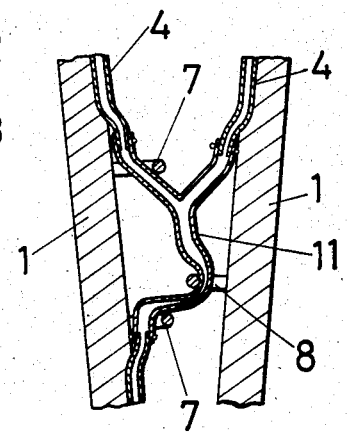

PAIR OF BIPOLAR DIATHERMY FORCEPS FOR SURGERY

BACKGROUND OF THE INVENTION

1. Field of the Invention

The present invention relates to a pair of bipolar diathermy forceps used for controlling hemorrhage at the operation, more specifically at the brain surgery.

2. Discussion of the Prior Art

With regard to the operation of controlling the hemorrhage of the tissue, possessing certain level of solidity, such as a skin, a muscle, and an intestinal tract, the traditional method has been that the metal forceps holds such a tissue and a thread ties the hemorrhage point thereof. So long as the cerebral surgery may be concerned, however, the cerebral tissue is extremely softer compared with the above-mentioned tissue so that neither holding the hemorrhage point by the forceps nor tying the same by the thread are possible. For this reason, the general method of controlling the hemorrhage, which neurosurgery has executed, is that the carried current provides the tissue with surgical diathermy, thereby stopping bleeding. As a diathermy device realizing the foregoing method, the bipolar diathermy forceps is available for use; two arms of this forceps serve electrically as + and − poles, respectively and only the tissue held by the forceps is adapted to be coagulated.

Nevertheless, the conventional forceps has several disadvantages that an adhesion of the tissue's portion, which is held by such a forceps so that it may be coagulated and provided with diathermic treatment, to the top edge of the forceps not only deteriorates the capability of coagulation but also leads to inability in an apparent view around the top edge of the forceps, whereby a pinpointing grasp of the hemorrhage point gets difficult. In order to overcome those disadvantages, the necessity of eliminating the adhered tissue by a knife and executing the operation of making the top edge of the forceps as clean as possible has no alternative but to interrupt the surgery for a while. Furthermore, if the hemorrhage takes place to the extreme limit, further disadvantage has been found in difficulty of controlling such a hemorrhage, because the blood, which is concurrently coagulated, is also adhered to the top edge of the forceps to a great extent.

Many attempts have been made to overcome these difficulties. King and Worpole (J. Neurosurg: Volume 37: August, 1972: Self-irrigation bipolar diathermy forceps) developed an instrument with a continuous saline drip through a fine metal tube mounted along one blade of the bipolar forceps. However, with this apparatus the saline flow continues even when the bipolar forceps is not in use. Dujovny, Vas and Osgood (Plastic & reconstructive surgery, November 1975: Bipolar jeweler's forceps with automatic irrigation, for coagulation in microsurgery) devised a combination of a pressure pump and an electromagnetic valve; the saline flow continues only when the bipolar forceps are in use. Sugita and Tsugane (J. Neurosurg: Volume 41: December, 1974: Bipolar coagulator with automatic thermocontrol) reported an all-transistorized bipolar coagulation consisting of a thermocouple concealed in the tip of the forceps. This apparatus avoids the adherence of tissue to the forceps tip by a thermocontrol mechanism, not by irrigation with saline.

SUMMARY OF THE INVENTION

The present invention aims at the provision of the bipolar diathermy forceps, which settles the foregoing conventional disadvantages, prevents the tissue being coagulated and provided with the diathermic treatment on the top of the forceps from being adhered to the top edge thereof, can be assuredly used for the surgery through enabling the discharged blood to be diluted.

An object of the invention is to provide an apparatus of the bipolar diathermy forceps used for surgery.

Other object of the invention is to provide a saline drip in bipolar diathermy.

Another object of the invention is to provide a tube embedded in both arms of a bipolar forceps and connected to the irrigating line, the irrigation is started when the forceps are closed and is stopped when they are open, automatically.

Still another object of the invention is to provide an on-off operation section which is inserted between two arms of the forceps, and which controls irrigation with saline by the movement of the arms.

In order to attain the foregoing purpose, the present invention forms the bipolar diathermy forceps for surgery possessing two arms, electrically insulated from each other, which, being adapted to keep opening their top edges, are in a position to give a diathermic treatment to the tissue including a blood vessel and the like, utilizing the carried current, when said top edges hold the tissue, being provided with the tube extending toward said top edges of the above-mentioned arms, while passing along a groove provided on either or both of the arms, a section to be elongated which is in contiguity to the above-mentioned groove on said top edges of the arms, an operational section, located on the middle part of the above-mentioned tube, which changes the interactive and positional relation between these two arms or manually adjusts such a relation, thereby opening or closing a hole on the tube, and a pouring section of liquid such as physiological saline solution and the like, which is located at the rear end of the above-mentioned tube.

Thus, when the forceps is not used, one arm thereof is in the state of being opened so that the flooding of the physiologic saline solution dose not take place. When the top edges of the forceps are closed such that they hold the tissue, the hole of the tube is opened so that the physiologic saline solution is introduced from the section to be elongated in contiguity to the groove of the top edge of the forceps and is dripped from the top end thereof. In case where the tissue is held by the top edges of the forceps and supplied with the current, the coagulation caused by the high frequency is conducted, whereby the control of hemorrhage is completed.

Since the present invention employs the foregoing formation, when holding the tissue such as the blood vessel by closing the forceps, the current is carried between the top edges of the forceps, the tissue being coagulated. At that time, an effluence of the physiologic saline solution which always take place, enables an adhesion of the tissue which has been provided with the diathermic treatment to the top edge of the forceps to be avoided almost with perfection. At the same time, a surplus of physiologic saline solution which has flown into the part provided with the surgery has an action of washing cleanly such a part as well as dillutes the hemorrhaging blood, so the surgery is made easier. The disadvantages founded in the conventional diathermic device can be fully settled. Namely, the conventional device prevents the normal current from being carried around the tips of arms which are coated with the coagulated blood. Because, the blood is high protein liquid which is coagulated before the tissue is done.

Since the section to be elongated in contiguity to the groove is terminated on this side of the top edge of the forceps so that the internal face thereof may get flat, the tissue is ensured to be held by the flat face, the effect of carrying the current is strengthened, and, in addition, the dripping of the physiologic saline solution is adequately induced by way of the section to be elongated. The coupling rings and the hook constituting the operational section cause the hold of the tube to be opened and closed in response to the change in the interactive and positional relation of two arms which takes place concurrently with the opening and closing of the forceps may be made toward a better and complicated operational section capable of being adjusted by the surgeon's free will, utilizing any attachment mounted thereto.

DESCRIPTION OF DRAWINGS

FIG. 1 is a front view of the embodiment according to the present invention,

FIG. 2 is a side view of the internal face of one arm,

FIG. 3 is a principally enlarged sectional view of the internal face of the arm, and FIG. 4 is a principally enlarged sectional view of another embodiment,

DESCRIPTION OF THE PREFERRED EMBODIMENT

The description of the embodiment may be made in conjunction with the drawings as follows:

1 is two arms as the forceps proper, being supported at their base by an insulation 2 and adapted always to be kept to open their top edges. These two arms, when using a microscope in the cerebral surgery, take a form of being bent downward from its part grasped by the surgeon's hand so that he may obtain as wide observing scope as possible at his hands. 3 is a terminal, connected to the high frequency power, which constitutes the bipolar diathermy forceps capable of coagulating the tissue including the blood vessel and the like, which is held by the top edges of the arms 1 and 1, for controlling hemorrhage therefrom. 4 is a tube, provided along the internal surface of the arm 1, which is somewhat embedded in the groove 5 formed on the arm 1. 6 is the tube made of synthetic resin compounded with silicon which makes a connection between the parts 4 and 4 of the tube, having a elasticity. 7 is a coupling ring striding over the above-mentioned synthetic resin made tube, being provided on each of two places between which an adequate spacing is made. 8 is an operational section, which comprises a hook mounted to the middle position between the coupling rings 7 and 7 on the arm 1 located at the side corresponding to the arm 1 provided with the coupling ring 7 and on which the synthetic resin made tube 6 is hung. This hook is functional in changing the interactive and positional relation between two arms 1 and 1. Namely, when releasing the fingers out of the forceps, two arms are opened, being elastically expanded such that the tube 6 is pulled so that the hole thereon is closed. When closing the forceps by the fingers, the stretching force in the hook is weakened, thereby opening the hole of the tube. 9 is the section to be elongated of the groove 5 formed on the arm 1, ranging from the top edge of the forceps up to the point more inner by ca. 1 cm therefrom. The rear end of the tube 4 is provided with a pouring section 10 of the liquid including the physiologic saline solution and the like.

FIG. 4 exemplifies illustratively the arrangement of providing the tubes 4 and 4 on both the sides of the arm 1. 10 is T-shaped tube made of synthetic resin compounded with silicon, which is suspended between the coupling rings 7 and 7 and the operational section 8, being adapted to close the hole of the tube by stretching the operational section 8, when opening the forceps. Although the drawing tentatively illustrates the state where the tube 4 is partially embedded in the groove 4 formed along inside of the arm 1, the practical mode may be not limited to such a formation; i.e. only if it does not give rise to any obstruction by the forceps against the surgeon's viewing scope to omit the groove, such an arrangement may be put into practice, mounting the tube to the outside of the arm 1 being also acceptable. In place of the operational section 8 comprising the coupling rings 7 and 7 and the hook, another type of operational section capable of opening and closing the hole of the tube 4 by means of pressurizing or sliding the same by the top of fingers may be basically plausible. Furthermore, the provision of the pouring section 10 of the physiologic saline solution on the rear end of the tube 4 may either conducted directly to the tube or by way of any attachment which is provided separately. If the tube is provided through the above-mentioned pouring section with a dripping apparatus of the physiologic salt solution which employs a system of natural dropping caused by gravity or a dripping speed changing gear, it is possible that as soon as the action of holding the tissue is started by closing the forceps, an adequate amount of physiologic saline solution flows out. And the effluence thereof is stopped, when the forceps is opened.

It has been apparent from the foregoing description that at the effluence of the physiologic saline solution, it drips from the top end of the tube 4 along the section to be elongated 9 in contiguity to the groove 5, the resultant thin layer of water provides the section of the tissue which has been given by the diathermic treatment and the forceps with a separation or a coating, and, in addition to the prevention of the tissue which has been coagulated and provided with the diathermic treatment from being adhered to the forceps by the interposition of bubbles (hydrolysis) generated by the carried current, such a layer ensures the current to be carried to the top edges of the forceps. The physiologic saline solution dilutes the blood flowing around, thereby making the surgery easy. It is because if the inner surface of the top edge of the arm is made flat, it brings a convenience to the effect of carrying the current as well as the development of executing the surgery, that the section to be elongated 9 in contiguity to the groove of the top end of the arm is terminated at the point more inner by ca. 1 cm from the top end thereof.

What is claimed is:

1. A pair of bipolar diathermy forceps for surgery comprising two arms, each having a base end and a tip at an opposite end thereof, insulator means for holding said base ends of said two arms, with said arms being electrically insulated from each other and with said tips at said other ends being unconnected to enable said tips to open and close, said arms having inside walls and at least one of said arms having a groove, said forceps further comprising a hollow tube for passing a saline solution therethrough extending from a position toward said base end of one of said two arms toward said tips along said inside walls of said arms and mounted along said groove, wherein said tube comprises an elongated section following said groove, an operational section disposed between said two arms, and an inlet section for supplying physiological saline through the hollow part of said tube, and means disposed on said inside walls of said arms in vicinity of said operational section of said tube for closing said hollow part of said tube when said tips are open, and for opening said hollow part of said tube when said tips are closed, wherein said means comprises a pair of coupling rings disposed on said inside wall of one arm for holding therein said operational section of said tube, and at least one hook disposed on said inside wall of the outer arm and positioned between said pair of coupling rings disposed on said one arm for holding therein said operational section of said tube, whereby said at least one hook on said other arm and said pair of coupling rings on said one arm act cooperatively on said operational section of said tube to open and close said hollow part thereof.

2. A pair of bipolar diathermy forceps for surgery, according to claim 1, wherein said tube comprises a stainless steel tube for a portion thereof passing along said groove of said arms, and a synthetic resin tube compounded with silicon for a portion thereof whereat said hollow part is opened and closed.

3. A pair of bipolar diathermy forceps for said surgery, according to claim 1, where said portion of said tube corresponding to said groove of said arms is partially embedded in a face of said inside wall of said arms.

* * * * *